(12) United States Patent
Adhiprakasha (10) Patent No.: US 9,297,773 B2
(45) Date of Patent: Mar. 29, 2016

(54) X-RAY FLUORESCENCE ANALYSIS OF THIN-FILM COVERAGE DEFECTS (71) Applicant: Intermolecular Inc., San Jose, CA (US)

(72) Inventor: Edwin Adhiprakasha, Mountain View, CA (US)

(73) Assignee: Intermolecular, Inc., San Jose, CA (US)

( * ) Notice: Subject to any disclaimer, the term of this patent is extended or adjusted under 35 U.S.C. 154(b) by 33 days.

(21) Appl. No.: 14/140,709

(22) Filed: Dec. 26, 2013

(65) Prior Publication Data

US 2015/0185170 A1 Jul. 2, 2015

(51) Int. Cl.
G01N 23/22 (2006.01)
C03C 15/00 (2006.01)
G01N 23/223 (2006.01)
B24B 37/013 (2012.01)
H01L 21/66 (2006.01)
C23F 1/00 (2006.01)

(52) U.S. Cl.
CPC .............. G01N 23/22 (2013.01); B24B 37/013 (2013.01); C03C 15/00 (2013.01); G01N 23/223 (2013.01); H01L 22/26 (2013.01); C23F 1/00 (2013.01); H01L 22/12 (2013.01)

(58) Field of Classification Search
None
See application file for complete search history.

(56) References Cited

U.S. PATENT DOCUMENTS 6,466,642 B1 * 10/2002 Meloni ............................ 378/44
8,486,727 B2    7/2013 Chen
2004/0029333 A1 *  2/2004 Matsukawa .................. 438/200
2005/0282300 A1   12/2005 Yun

OTHER PUBLICATIONS

Yongliang et al.; Selective wet etch of a TaN metal gate with an amorphoussilicon hard mask; Apr. 18, 2010; Z-Not Available.
Lee et al.; Band alignment of InGaZnO4Si interface by hard xray photoelectron spectroscopy; Aug. 9, 2012; American Institute of Physics.
Helmholtz-Berlin.DE; Experimental setup for in situ EDXRDXRF at Bessy II; ; http://www.helmholtz-berlin.de/forschung/enma/technologie/research-activities/semiconductors/setup_en.html; Mar. 21, 2013.

* cited by examiner

*Primary Examiner* — Jiong-Ping Lu (57) ABSTRACT

X-ray fluorescence (XRF) monitoring of characteristic peaks while etching thin-film layers can reveal coverage defects and thickness nonuniformity in the top film. To measure coverage and uniformity while screening candidate layer materials and processes, the candidate layers may be formed above an underlayer of a different composition. A wet etchant that selectively etches the underlayer faster than the candidate layer is applied to the candidate layer, and the XRF spectrum is monitored. Pinholes, cracks, islands, and nonuniform thickness in the candidate layer produce characteristic features in the time-dependent behavior of XRF peaks from the underlayer and/or the candidate layer. "Etch/XRF" tests can be used to rapidly and objectively identify the most uniform contiguous candidate layers to advance to further screening or production. XRF may also be calibrated against a known thickness indicator to detect the approach of a desired endpoint in an etch process.

18 Claims, 8 Drawing Sheets

X-RAY FLUORESCENCE ANALYSIS OF THIN-FILM COVERAGE DEFECTS

BACKGROUND

Related fields include evaluation and screening of candidate materials and processes for thin-film stacks and devices.

The performance of advanced thin-film devices is often sensitive to thickness of individual layers. Tolerances on average film thickness, thickness uniformity, and continuity of coverage (i.e., absence of "pinholes," cracks, or other gaps in the layer that constitute "coverage defects") may accordingly be very tight. Measurement of these parameters, including real-time monitoring during fabrication processes, can be challenging. In particular, visual evaluation of coverage defects can be time-consuming and prone to errors.

When selecting materials and processes for new or improved devices, coverage properties are often a critical factor. Therefore, a need exists for a rapid, reliable analysis method for coverage defects in candidate films.

When removing material from a device being fabricated (e.g., by etching), a particular thickness of a specific material may need to be left in place. Therefore, a need exists for a reliable method of monitoring the composition and thickness of the topmost layers in a device film stack.

SUMMARY

The following summary presents some concepts in a simplified form as an introduction to the detailed description that follows. It does not necessarily identify key or critical elements and is not intended to reflect a scope of invention.

Some embodiments of methods for screening candidate materials and processes for thin films include forming an underlayer over a substrate, forming a candidate layer over the underlayer, exposing the substrate to a selective etchant known to etch the underlayer material more rapidly than the candidate layer material, and monitoring the X-ray fluorescence (XRF) spectrum from the substrate before and after the etching. In some embodiments, the etching may be paused at one or more points to allow XRF measurements. In some embodiments, the XRF spectrum is collected during the etching (e.g., when the etchant sufficiently transmits both the incident and fluorescent X-ray wavelengths). Changes in the XRF spectrum during the etching reveal the presence, severity, and nature of coverage defects. For example, islands, such as those that may be formed by agglomeration during annealing or other deficiencies of adhesion, may be distinguished from pinholes, cracks, or uncovered sidewalls of 3D structures. Non-uniformity of thickness, composition, or density may be detected in layers that completely cover underlying layers or structures. Some embodiments of these methods can be used to analyze layers formed over an entire substrate by conventional processing, or to analyze layers formed in multiple-site-isolated regions on a substrate by high-productivity combinatorial (HPC) processing.

Some embodiments of methods for detecting an endpoint of a material-removal process for one or more thin films may include etching the film or stack past a desired endpoint while monitoring the XRF spectrum and simultaneously monitoring the thickness by a known independent method, such as interferometry or ellipsometry, that indicates when the removal process reaches its endpoint. Alternatively, the calibration process may use the correlation between changes in the known indicator and changes in the XRF spectrum, whether or not the etching reaches or passes the endpoint. Comparison of the monitoring results provides a calibration of the XRF measurement so that XRF can be used alone to detect when the material removal reaches its endpoint on subsequent similar substrates.

BRIEF DESCRIPTION OF DRAWINGS

The accompanying drawings may illustrate examples of concepts, embodiments, or results. They do not define or limit the scope of invention. They are not drawn to any absolute or relative scale. In some cases, identical or similar reference numbers may be used for identical or similar features in multiple drawings.

DETAILED DESCRIPTION OF EXAMPLE EMBODIMENTS

A detailed description of one or more example embodiments is provided below. To avoid unnecessarily obscuring the description, some technical material known in the related fields is not described in detail. Semiconductor fabrication generally requires many other processes before and after those described; this description omits steps that are irrelevant to, or that may be performed independently of, the described processes.

Unless the text or context clearly dictates otherwise: (1) By default, singular articles "a," "an," and "the" (or the absence of an article) may encompass plural variations; for example, "a layer" may mean "one or more layers." (2) "Or" in a list of multiple items means that any, all, or any combination of less than all the items in the list may be used in the invention. (3) Where a range of values is provided, each intervening value is encompassed within the invention. (4) "About" or "approximately" contemplates up to 10% variation. "Substantially equal," "substantially unchanged" and the like contemplate up to 5% variation.

"Horizontal" defines a plane parallel to the plane or surface of the substrate. "Vertical" shall mean a direction perpendicular to the horizontal as previously defined. "Above," "below," "bottom," "top," "side" (e.g. sidewall), "higher," "lower," "upper," "over," and "under" are defined with respect to the horizontal plane. "On" indicates direct contact; "above" and "over" allow for intervening elements. "On" and "over" include conformal configurations covering feature walls oriented in any direction.

"Substrate," as used herein, may mean any workpiece on which formation or treatment of material layers is desired. Substrates may include, without limitation, silicon, germanium, silica, sapphire, zinc oxide, SiC, AlN, GaN, Spinel, coated silicon, silicon on oxide, silicon carbide on oxide, glass, gallium nitride, indium nitride and aluminum nitride, and combinations (or alloys) thereof. The term "substrate" or "wafer" may be used interchangeably herein. Semiconductor wafer shapes and sizes can vary and include commonly used round wafers of 50 mm, 100 mm, 150 mm, 200 mm, 300 mm, or 450 mm in diameter.

"Film" and "layer" are synonyms representing a portion of a stack, and may mean either a single layer or a portion of a stack with multiple sub-layers (e.g., a nanolaminate). As used herein, "etch" shall mean any chemical removal of solid material, whether or not the material is being removed in any specific pattern. "Conformal" shall mean a step coverage of at least 90%.

As used herein, "site-isolated region" (SIR) shall mean one or more regions on a substrate that are separated and used for the evaluation of different materials or process parameters. The SIR may have any convenient shape, e.g., circular, rectangular, elliptical, wedge-shaped, etc. In the semiconductor field, a region may include, for example, a test structure, single die, multiple dies, portion of a die, or other defined portion of substrate. The SIRs can be formed using many different methods such as scribing, deposition through a shadow mask, deposition using isolated deposition heads, lithography, and the like. Where one region is processed at a time, adjacent regions are generally protected from any exposure that would alter the substrate surface in a measurable way. Site isolation may provide complete isolation between regions or relative isolation between regions.

Figure 1:
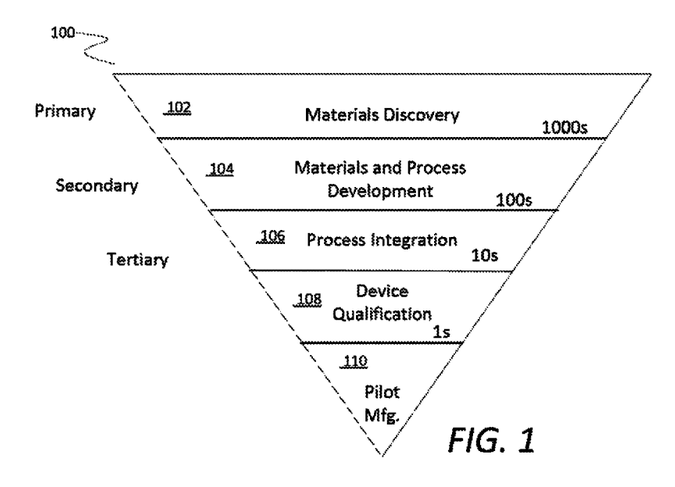
FIG. 1 is a schematic diagram of device development using primary, secondary, and tertiary screening methods that include HPC processing with or without conventional (full-substrate) processing.

FIG. 1 is a schematic diagram of device development using primary, secondary, and tertiary screening methods that include HPC processing with or without conventional (full-substrate) processing. The diagram 100 illustrates how the selection of the most promising candidates at each stage decreases the relative number of combinatorial processes that need to be run in the next stage. Generally, a large number of processes are performed during a primary screening stage. Based on the primary-screening results, a subset of the most promising candidates is selected and subjected to a secondary screening stage. Based on the secondary-screening results, a smaller subset of most-promising candidates is selected and subjected to a tertiary screening stage, and so on. Feedback from later stages to earlier stages can be used to refine the success criteria and provide better screening results.

For example, thousands of materials may be evaluated during a materials discovery stage 102, a primary screening stage. Techniques for this stage may include, e.g., dividing substrates into coupons and depositing materials on each of the coupons. Materials, deposition processes, or both may vary from coupon to coupon. The processed coupons are then evaluated using various metrology tools, such as electronic testers and imagers. A subset of promising candidates is advanced to the secondary screening stage, materials and process development stage 104.

Hundreds of materials (i.e., a magnitude smaller than the primary stage) may be evaluated during the materials and process development stage 104, which may focus on finding the best process for depositing each of the candidate materials. A subset of promising candidates is selected to advance to the tertiary screening stage, process integration stage 106.

Tens of material/process pairs may be evaluated during the process integration stage 106, which may focus on integrating the selected processes and materials with other processes and materials. A subset of promising candidates is selected to advance to device qualification stage 108.

A few candidate combinations may be evaluated during the device qualification stage 108, which may focus on the suitability of the candidate combinations for high volume manufacturing. These evaluations may or may not be carries out on full-size substrates and production tools. Successful candidate combinations proceed to pilot manufacturing stage 110.

The schematic diagram 100 is an example. The descriptions of the various stages are arbitrary. In other embodiments of HPC, the stages may overlap, occur out of sequence, or be described or performed in other ways.

HPC techniques may arrive at a globally optimal process sequence by considering the interactions between the unit manufacturing processes, the process conditions, the process hardware details, and material characteristics of components. Rather than only considering a series of local optima for each unit operation considered in isolation, these methods consider interaction effects between the multitude of processing operations, influenced by the order in which they are performed, to derive a global optimum sequence order.

HPC may alternatively analyze a subset of the overall process sequence used to manufacture a device; the combinatorial approach may optimize the materials, unit processes, hardware details, and process sequence used to build a specific portion of the device. Structures similar to parts of the subject device structures (e.g., electrodes, resistors, transistors, capacitors, waveguides, or reflectors) may be formed on the processed substrate as part of the evaluation.

While certain materials, unit processes, hardware details, or process sequences are varied between different site-isolated regions of the substrate, other parameters (e.g., composition or thickness of the layers or structures, or the unit process action such as cleaning, surface preparation, deposition, surface treatment, or the like) are kept substantially uniform across the substrate. Furthermore, while different materials or unit processes may be used for corresponding layers or steps in the formation of a structure in different regions of the substrate, the application of each layer or the use of a given unit process may be substantially consistent among the regions. Thus, aspects of the processing may be uniform within a region (inter-region uniformity) or between regions (intra-region uniformity), as desired.

The result is a series of regions on the substrate that contain structures or unit process sequences that have been uniformly applied at least within that region and, as applicable, across multiple regions. This process uniformity allows comparison of the properties within and across the different regions so that the variations in test results are due to the intentionally varied parameter (e.g., material, unit process, unit process parameter, hardware detail, or process sequence) and not to a lack of process uniformity. The positions of the site-isolated regions can be defined as needed, but are preferably systematized for ease of tooling and design of experiments. The number, location, and variants of structures in each region preferably enable valid statistical analysis of test results within and between regions.

Figure 2:
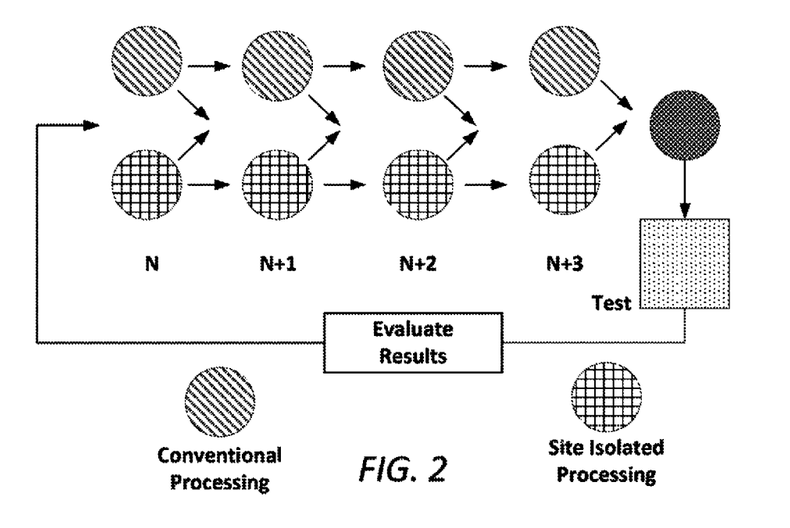
FIG. 2 is a simplified schematic diagram illustrating a general methodology for combinatorial process sequence integration that includes site-isolated processing, conventional processing, or both.

FIG. 2 is a simplified schematic diagram illustrating a general methodology for combinatorial process sequence integration that includes site-isolated processing, conventional processing, or both. For example, the substrate may be initially processed by conventional process N, then by site isolated process N+1. During site isolated processing, an HPC module may be used, such as the HPC module described in U.S. Pat. No. 8,084,400. The substrate may then be processed by site isolated process N+2, and thereafter by conventional process N+3, followed by testing and evaluation of test results. The testing may measure physical, chemical, acoustic, magnetic, electrical, optical, etc. properties. From this evaluation, a particular process from the various site isolated processes (e.g. from steps N+1 and N+2) may be selected and fixed so that additional combinatorial process sequence integration may be performed using site isolated processing for either process N or N+3. For example, a next process sequence can include processing the substrate using site isolated process N, conventional processing for processes N+1, N+2, and N+3, with testing performed thereafter.

Various other combinations of conventional and combinatorial processes can be included in the processing sequence. The combinatorial process sequence integration can be applied to any desired segments and/or portions of an overall process flow. Characterization can be performed after each process operation and/or series of process operations within the process flow as desired. Furthermore, the flows can be applied to entire monolithic substrates, or portions such as coupons.

Parameters which can be varied between site-isolated regions include, but are not limited to, process material amounts, reactant species, process temperatures, process times, process pressures, process flow rates, process powers, reagent compositions, the rates at which the reactions are quenched, atmospheres in which the processes are conducted, order in which materials are deposited, hardware details including gas or liquid distribution assemblies, etc. These process parameter examples are not an exhaustive list; numerous other process parameters used in device manufacturing may also be varied.

Within a region, the process conditions may be kept substantially uniform, in contrast to gradient processing techniques which rely on the inherent non-uniformity of the material deposition. That is, each site-isolated region may be processed in a substantially uniform way, even though the materials, processes, and process sequences may vary from region to region over the substrate. Thus, the testing will find optima without interference from process variation differences between processes that are meant to be the same. Regions may be contiguous, or may overlap, or may be surrounded by unprocessed margins. Where regions are contiguous or overlapping, the materials or process interactions in the overlap may be uncertain. However in some embodiments at least 50% of the area within a region is uniformly processed and all testing can be done in that uniform area. Experiments may be designed to allow potential overlap only between materials or processes that will not adversely affect the result of the tests.

Combinatorial processing can be used to determine optimal processing parameters (e.g., time, concentration, temperature, stirring rate, etc.) of wet processing techniques such as wet etching, wet cleaning, rinsing, and wet deposition techniques (e.g., electroplating, electroless deposition, chemical bath deposition, dip coating, spin coating, and the like).

Figure 3A:
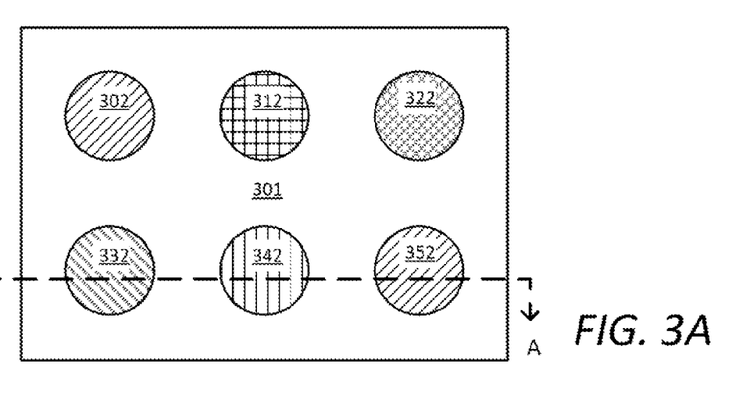
FIGS. 3A and 3B are two conceptual views of a combinatorially-processed substrate.
Figure 3B:
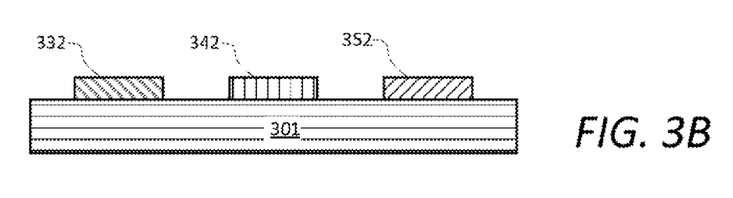

FIGS. 3A and 3B are two conceptual views of a combinatorially-processed substrate. T. FIG. 3A is a top view of substrate 301 showing 6 site-isolated regions 302, 312, 322, 332, 342, and 352. Although substrate 301 is rectangular in the illustration, any suitable substrate shape such as circular, square, or polygonal may also be used in some embodiments. Although the site-isolated regions 302, 312, 322, 332, 342, and 352 are shown as separated from each other by unprocessed areas of substrate 301, in some embodiments the site-isolated regions may be contiguous or partially overlapping. Some of the site-isolated regions may be chosen to be processed identically (as regions 302 and 352 are shown here with identical shading) to test the consistency of the results on different regions of the same substrate.

FIG. 3B is a sectional view through section line A-A of FIG. 3A showing different films formed on site-isolated regions 332, 342, and 352. The regions could alternatively have identical (or no) films formed, and the variation could instead be in the cleaning, etching, polishing, or some other treatment of the different regions.

Figure 4A:
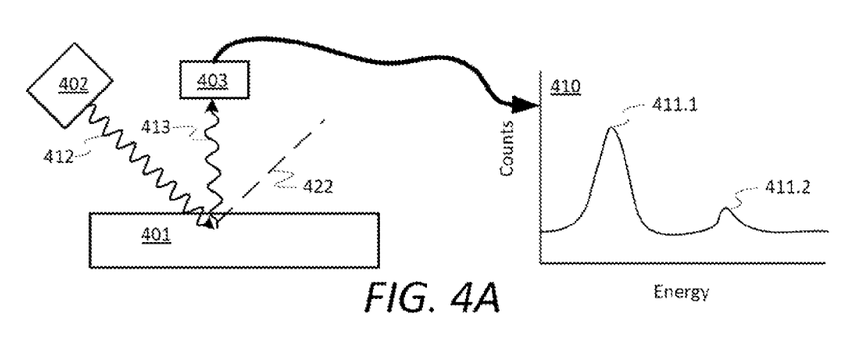
FIGS. 4A and 4B illustrate XRF.
Figure 4B:
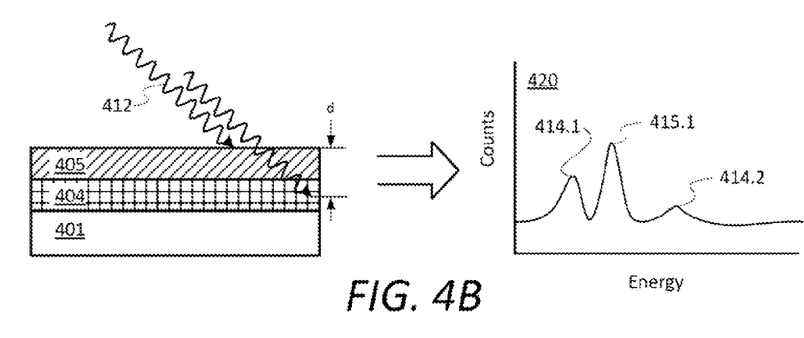

FIGS. 4A and 4B illustrate XRF. In FIG. 4A, a block diagram shows an XRF apparatus and an example spectrum. X-ray source 402 irradiates substrate 401 with incident X-radiation 412. In some embodiments, X-ray source 402 may include an X-ray generator tube, a synchrotron, or radioactive material. In some embodiments, incident radiation 412 may also include gamma radiation; "incident X-radiation" will be used herein as a generic term of convenience that does not exclude gamma radiation. Without being restricted to any particular theory, it is believed that an incident X-ray photon striking an atom on substrate 401 ejects an electron from an inner orbital of the atom. An electron from an outer orbital of the atom "moves" (changes state) to fill the vacancy created by the ejected electron. Because the inner orbitals are lower in energy than the outer orbitals, the energy lost in the vacancy-filling transition exits the atom as an emitted X-ray photon (the "fluorescence.") Fluorescent X-radiation 413 is detected by XRF detector 403 and spectrally analyzed, for example as a graph 410.

A transition between an inner orbital and free space requires more energy than a transition between the inner orbital and an outer orbital of the same atom. Therefore, fluorescent X-radiation 413 generally has lower energy (longer wavelength) than incident X-radiation 412. Moreover, although incident X-radiation 412 may be concentrated into a focused or collimated beam, fluorescent X-radiation 413 is emitted through a wide range of angles. Taking advantage of this, XRF detector 403 may be positioned out of the reflection path 422, so that the signal is not contaminated with reflections of incident X-radiation 412. XRF detector 403 may be, for example, a proportional counter, a p-i-n diode, a silicon-lithium (Si(LI) or germanium-lithium (Ge(Li)) detector, or a silicon drift detector (SDD).

Through the XRF control and signal-analysis instrumentation, the signal reaching XRF detector 403 is converted to a spectrum, e.g. graph 410, with energy (typically in keV) on the x-axis and counts (detected intensity) on the y-axis. In some embodiments, wavelength may be the x-axis. Peaks 411.1 and 411.2 are characteristic of an element in the material of substrate 401. Multiple peaks may occur for the same element when incident X-radiation 412 ejects electrons from different orbitals (K, L, M) or when the vacancy-filling transitions differ from atom to atom (e.g., some K vacancies are filled from L, and other K vacancies are filled from M). Moreover, each element in a compound contributes at least one peak; for example, if substrate 401 were a silicon-germanium alloy, peak 411.1 might represent the silicon and peak 411.2 might represent the germanium.

In FIG. 4B, substrate 401 is coated with layers 404 and 405. Incident X-radiation 412 may be absorbed near or at the surface of top layer 405 or it may penetrate to any depth down to a limiting depth d. An irradiation volume of the X-rays within substrate 401 is defined by limiting depth d, the incident spot size, and the angle of convergence or divergence of the incident X-ray beam. Limiting depth d may be somewhat material-dependent, but in general, for materials used in semiconductor fabrication and the XRF instruments used to measure them, d is on the order of 50-500 nm.

In the illustration, limiting depth d includes the entire thickness of top layer 405 and some of the thickness of underlayer 404 under top layer 405, but it does not reach substrate 401 under underlayer 404. The number of counts in each characteristic peak in an XRF spectrum is directly related to the amount of each corresponding element in the material being measured. In graph 420, peaks 415.1 from top layer 405 and peaks 414.1 and 414.2 from underlayer 404 are visible. However, neither of the peaks 411.1 and 411.2 from substrate 401 is visible because, being farther than limiting depth d below the top surface, substrate 401 is not reachable by incident X-radiation 412. Moreover, although layers 404 and 405 are actually about the same thickness, peak 415.1 is stronger than either peak 414.1 or peak 414.2 because limiting depth d includes all of top layer 405 but only part of underlayer 404.

If the thicknesses of top layer 405 were to change, so would the spectrum 420. If top layer 405 became thicker, limiting depth d would approach and eventually pass the interface between top layer 405 and underlayer 404, so that peaks 414.1 and 414.2 would be progressively attenuated and eventually disappear altogether. If, instead, top layer 405 became thinner, limiting depth d would extend farther and farther into underlayer 404. Peak 415.1 would become attenuated while peaks 414.1 and 414.2 would become amplified, and when d began to extend into substrate 401, peaks 411.1 and 411.2 would emerge. As long as at least two different materials are within the limiting depth d from a top surface, the XRF spectrum may accurately indicate the progress of deposition (thickening) or etching (thinning) of the top layer.

Figure 5A:
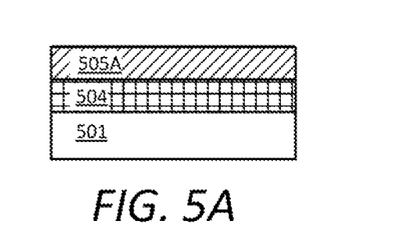
FIGS. 5A-5F conceptually illustrate coverage differences in top layers.
Figure 5B:
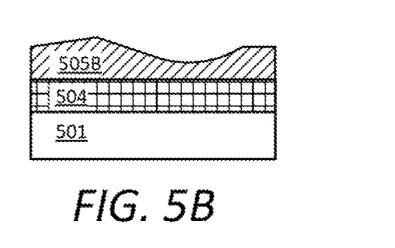
Figure 5C:
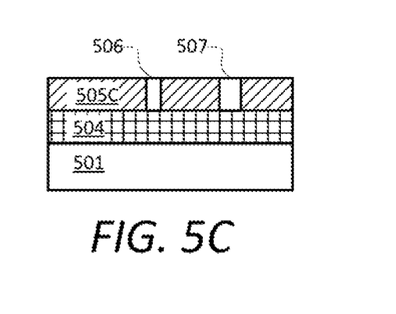
Figure 5D:
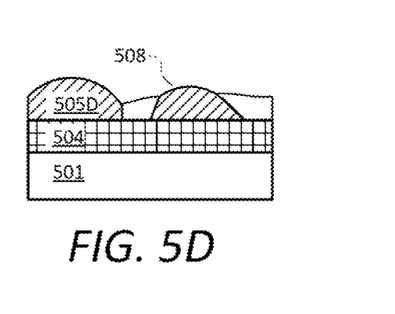
Figure 5E:
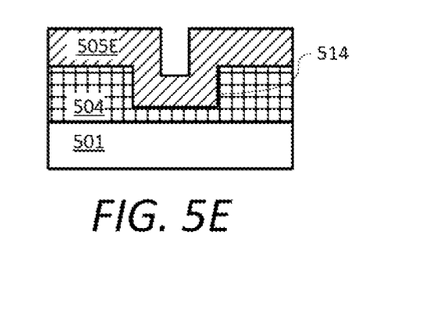
Figure 5F:
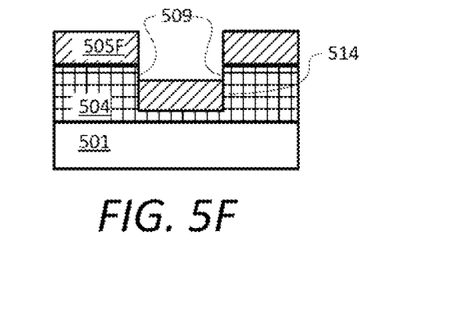

FIGS. 5A-5F conceptually illustrate coverage differences in top layers. In FIG. 5A, layer 505A completely covers underlayer 504 with uniform thickness. In FIG. 5B, layer 505B completely covers underlayer 504, but the thickness is not uniform. In FIG. 5C, layer 505C mostly covers underlayer 504, but there is a pinhole 506 and a crack 507 that expose small areas of underlayer 504. In FIG. 5D, layer 505D is not contiguous, but has formed islands 508 with exposed areas of underlayer 504 between them. In FIG. 5E, layer 505E covers underlayer 504 with uniform thickness, including uniform step coverage in trench 514. In FIG. 5F, layer 505F covers the bottom of trench 514 but leaves gaps 509 on the trench sidewalls, in which layer 504 is exposed.

The following examples are simplified by giving each layer a single characteristic peak; in practice, they may each have more than one peak.

Figure 6A:
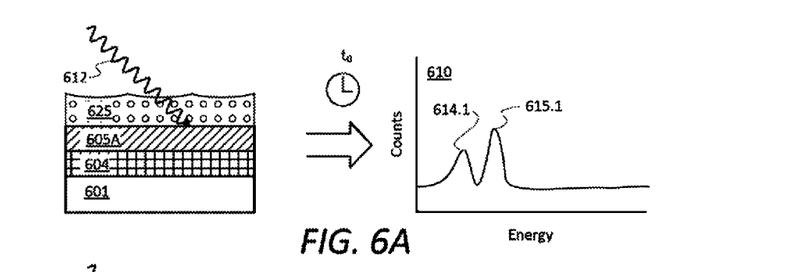
FIGS. 6A and 6B conceptually illustrate an etch-XRF test of a uniform, contiguous top layer.
Figure 6B:
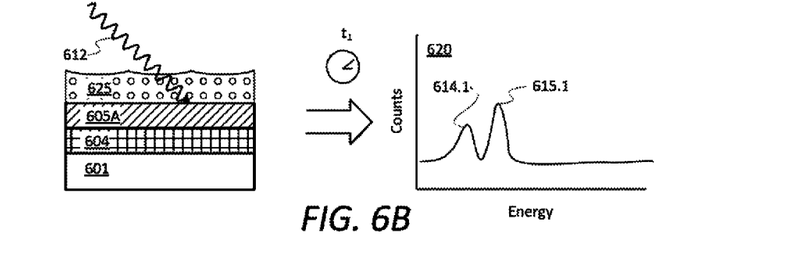

FIGS. 6A and 6B conceptually illustrate an etch-XRF test of a uniform, contiguous top layer. In FIG. 6A, substrate 601 has a uniform, contiguous top layer 605A (similar to top layer 505A in FIG. 5A) over an underlayer 604. At time $t=t_0$, top layer 605A is exposed to a selective wet etchant 625 known to etch underlayer 604 but not top layer 605A, and the XRF spectrum is graph 610, showing a strong initial peak 615.1 for top layer 605A and a weaker initial peak 614.1 for underlayer 604.

In FIG. 6B, the XRF spectrum is measured again at time $t_1$, after exposure to the selective wet etchant for time t. Graph 620 is substantially identical to graph 610 because wet etchant 625 cannot etch layer 605A and cannot reach underlayer 604.

Those skilled in the art will readily understand that the same type of spectral behavior would be seen if the top layer was the type of uniform, contiguous conformal layer 505E illustrated in FIG. 5E. The wet etchant would have no effect because it would be blocked everywhere from the underlayer 504, which it can etch, by layer 505E, which it cannot etch.

Figure 7A:
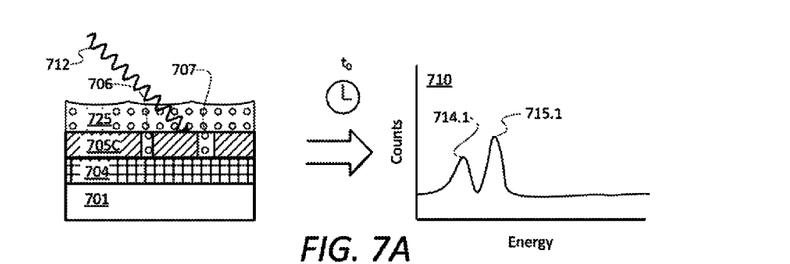
FIGS. 7A and 7B conceptually illustrate an etch-XRF test of a top layer with pinholes or cracks.
Figure 7B:
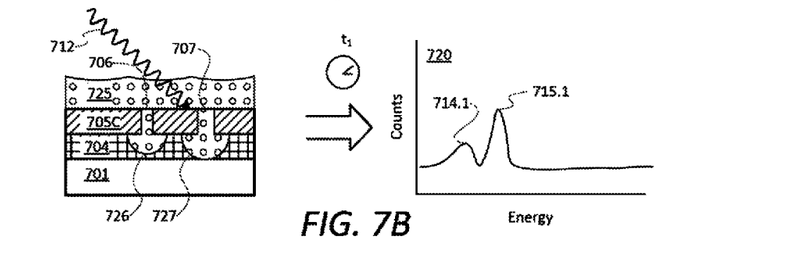

FIGS. 7A and 7B conceptually illustrate an etch-XRF test of a top layer with pinholes or cracks. In FIG. 7A, substrate 701 has a top layer 705A with pinhole 706 and crack 707 (similar to top layer 505C in FIG. 5C) over an underlayer 704. At time $t=t_0$, top layer 705C is exposed to a selective wet etchant 725 known to etch underlayer 704 but not top layer 705C, and the XRF spectrum is graph 710, showing a strong initial peak 715.1 for top layer 705C and a weaker initial peak 714.1 for underlayer 704. Note that wet etchant 725 is sufficiently non-viscous to flow into pinhole 706 and crack 707, at the bottoms of which underlayer 704 is exposed.

In FIG. 7B, the XRF spectrum is measured again at time $t_1$, after exposure to the selective wet etchant for time t. In graph 720, peak 714.1 for underlayer 704 is notably smaller in graph 720 than in graph 710 because wet etchant 725 etched large, undercut pits 726, 727 into underlayer 704 from the bottoms of pinhole 706 and crack 707. As a result, there is now less material from layer 704 within the volume irradiated by incident X-radiation 712, and therefore its peak 714.1 is diminished. However, peak 715.1 for top layer 705C is essentially unchanged from graph 710 because wet etchant 725 does not affect top layer 705C. Top layer 705C, being mostly contiguous, essentially holds itself together above the undercuts, though some parts may collapse into the pits.

Those skilled in the art will readily understand that the same type of spectral behavior would be seen if the top layer had the type of sidewall gaps illustrated in FIG. 5F. The selective etchant would carve undercut pits into layer 504 from the sidewall gaps 509 in top layer 505F; the amount of underlayer 504 material in the X-ray irradiated volume would decrease while the amount of top layer 505 material remained constant; therefore, the peak(s) characteristic of layer 504 would diminish while those characteristic of layer 505 would not change.

Figure 8A:
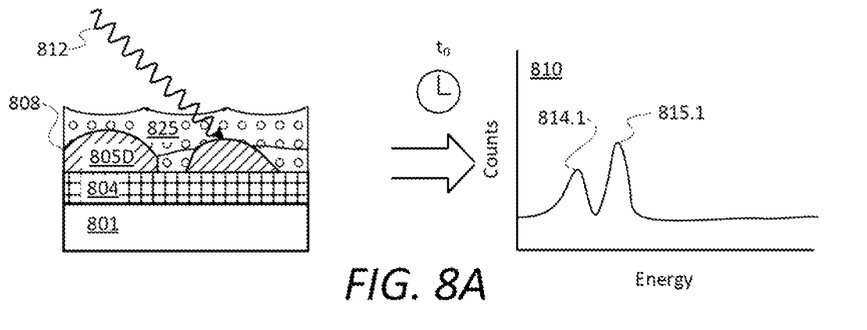
FIGS. 8A and 8B show an etch-XRF test of a top layer with islands.
Figure 8B:
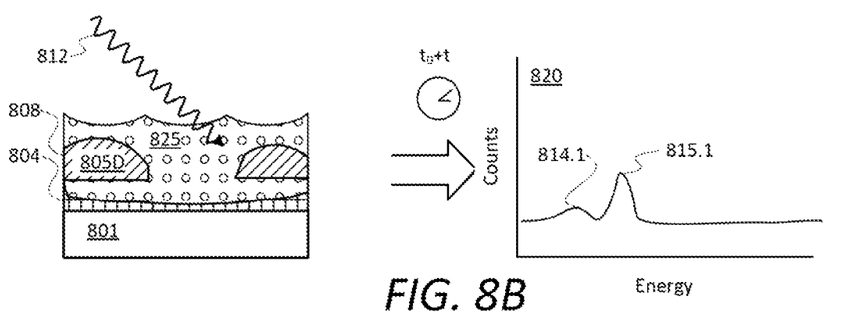

FIGS. 8A and 8B show an etch-XRF test of a top layer with islands. For example, layers that agglomerate after annealing may form islands, but other adhesion problems may have similar results. In FIG. 8A, substrate 801 has a top layer 805D with islands 808 (similar to top layer 505D in FIG. 5D) over an underlayer 804. At time $t=t_0$, top layer 805A is exposed to a selective wet etchant 825 known to etch underlayer 804 but not top layer 805A, and the XRF spectrum is graph 810, showing a strong initial peak 815.1 for top layer 805A and a weaker initial peak 814.1 for underlayer 804. Wet etchant 825 is sufficiently non-viscous to flow into the interstices between islands 808, where underlayer 804 is exposed. In FIG. 8B, the XRF spectrum is measured again at time $t_1$, after exposure to the selective wet etchant for time t. In graph 820, peak 814.1 for underlayer 804 is diminished because etchant 825, working from the interstices between the islands, undercut top layer 805D and etched away underlayer 804 where it interfaced islands 808. In addition, peak 815.1 for top layer 805D is also diminished because, once islands 808 were completely undercut, neither underlayer 804 nor other parts of top layer 805D held islands 808 in place. Islands 808, floating freely in wet etchant 825, floated partially out of the X-ray beam, providing less material from layer 805D within the irradiation volume.

Figure 9:
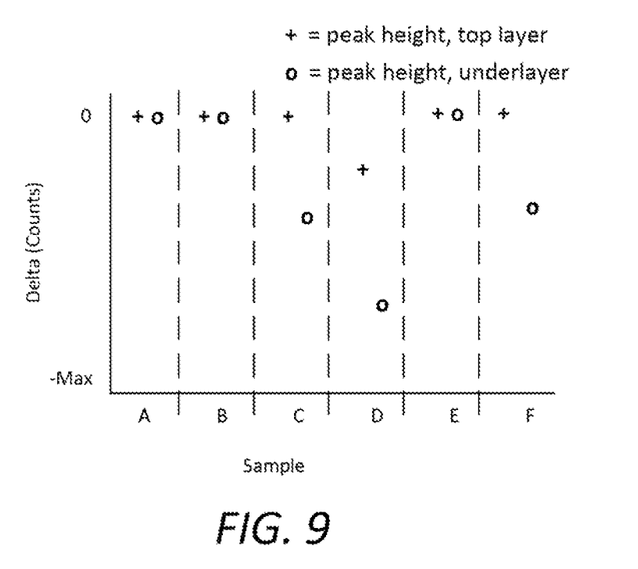
FIG. 9 is a simulated graph of results from samples tested by an etch-XRF method.

FIG. 9 is a simulated graph of results from samples tested by an etch-XRF method. The samples may be in different site-isolated regions on a single substrate, or they may be on different substrates. All the samples used the same underlayer composition and the same selective wet etchant, but at least some of the top layers differed between the samples. The top layers may differ in (by way of non-limiting example) material composition, thickness, deposition method, pre- or post-treatment, other processes, or process sequence. In some embodiments, the underlayer may include 3D structures such as trenches, vias, ridges, or pillars so that step coverage of the top layers can be compared.

The sample identifiers A, B, C, D, E, F correspond to top layers with the characteristics shown in FIGS. 5A, 5B, 5C, 5D, 5E, and 5F respectively. Delta (Counts) represents the change in XRF peak height between the beginning and the end of the etch process. The "+" data points represent the top-layer peak and the "o" data points represent the underlayer peak. For simplicity, only two tracked peaks are plotted, but any number of peaks may be tracked in practice. The wet etchant was chosen to etch the underlayer material and preserve (not etch) all of the top layer materials.

Samples A, B, and E had delta(counts)=0 for both peaks. Even though B had non-uniform thickness (see FIG. 5B), it had no breaks through which the etchant could reach the underlayer. Samples A, B, and E therefore "pass" this screening test and may be selected for the next stage of screening.

Sample C (with pinholes and cracks) and sample F (with sidewall gaps) had delta(counts)=0 for the top layer and a finite negative delta(counts) for the underlayer, because the etchant reached the underlayer through the coverage defects but the top layer remained contiguous. Sample D (with islands) had finite negative delta(counts) for both the top layer and the underlayer, because the etchant etched the underlayer enough to detach the islands, which floated. Samples C, D, and F therefore "fail" this screening test and may be unselected for the next stage of screening. Furthermore, some sidewall-gap samples might behave like islanded samples if isolated sections of top layer on the tops or bottoms of 3D features become detached and float in the etchant.

Compared to a visual inspection of top-layer defects, analysis of this graph takes less time, is less subjective, and may be quantitatively more reliable. However, this test produced the same results for contiguous but non-uniform layer of sample B as for the contiguous uniform layers of samples A and E. To discover the non-uniformity of samples like B, the samples may be tested again with a different wet etchant that etches both the top layer and the underlayer, but etches the top layer more slowly than the underlayer.

Thus in some embodiments of etch/XRF testing, XRF measurements are done before and after the etching. In some embodiments, the etching may be paused at one or more points to allow additional XRF measurements. In some embodiments, the XRF spectrum is collected during the etching (e.g., when the etchant sufficiently transmits both the incident and fluorescent X-ray wavelengths).

Choice of the underlayer, and of the peaks to monitor, are a factor in the clarity of information provided by etch-XRF tests. To accurately detect when the etchant reaches the underlayer, the top layer and the underlayer should each have at least one XRF peak at a different energy or wavelength from any peak produced by the other layer.er. For example, if the top layer is tantalum silicon nitride, silicon nitride may not be an optimal choice for an underlayer because its only peaks (from silicon and nitrogen) are also produced by the top layer. If, instead, silicon oxide is used as the underlayer, the monitored peaks could be the tantalum and/or nitrogen from the top layer and the oxygen in the underlayer. Alternatively, hafnium silicon nitride could be used as the underlayer; the hafnium peak from the bottom layer and the tantalum peak from the top layer could be monitored. Additionally, if the test may etch through the underlayer to a substrate or other lower stratum, the lower stratum should also not produce a peak that overlaps with measured peaks from the top layer or the underlayer. Often, the availability of selective wet etchants will also weigh against choosing top layers and underlayers with compositions that are highly similar. Resolution of the XRF measuring instrument is also a consideration; the peaks measured for each of the layers should be clearly distinguishable from any peak from the other layer.

Figure 10A:
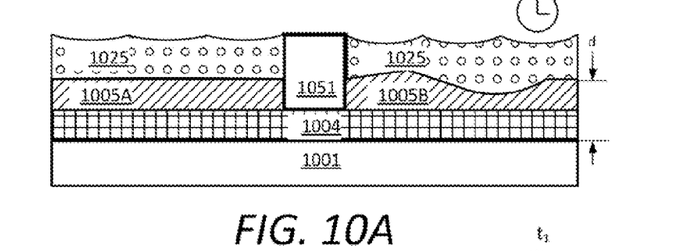
FIGS. 10A-10D conceptually illustrate an etch-XRF test sensitive to thickness variation in a contiguous top layer.

FIGS. 10A-10D conceptually illustrate an etch-XRF test sensitive to thickness variation in a contiguous top layer. In FIG. 10A, at time $t_0$, top layers 1005A and 1005B are exposed to wet etchant 1025. Wet etchant 1025 etches underlayer 1004 and top layers 1005A and 1005B, but the etch rate for underlayer 1004 is significantly higher (e.g., greater than about 1.3× higher) than the etch rate for top layers 1005A and 1005B. Substrate 1001 is blanket-coated with underlayer 1004. Uniform top layer 1005A and non-uniform top layer 1005B are shown as being formed in site-isolated regions separated by barrier 1051. Barrier 1051 could be part of an apparatus, such as a protective chuck or reactor wall; alternatively, barrier 1052 could be created by pressurized gas or a ridge fabricated on the substrate, or could be an etch-stop area that protects the part of underlayer 1004 between the site-isolated regions but allows etchant 1025 to flow freely between the regions. Alternatively, top layers 1005A and 1005B could be on separate substrates. Each of the top layers is separately monitored by XRF.

Figure 10B:
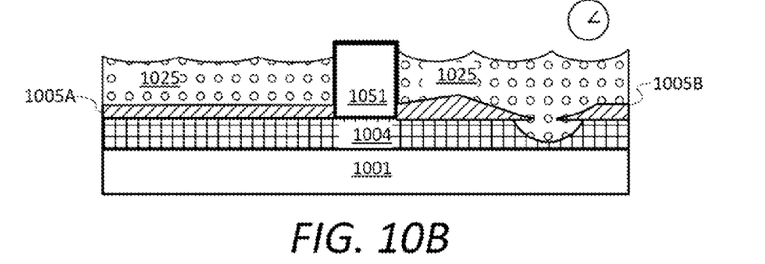

In FIG. 10B, at a later time $t_1$, etchant 1025 is still slowly etching uniform top layer 1005A and has not yet reached the underlying part of underlayer 1004. In the XRF measurement, the peak for top layer 1005A will be diminished from its height at $t_0$, but the peak for the part of underlayer 1004 underneath 1005A will be unchanged. Meanwhile, etchant 1025 has broken through a thin spot in nonuniform top layer 1005B and has begun to rapidly etch the underlying part of underlayer 1004, carving out an undercut pit. In the XRF measurement, the peaks for both layers will be diminished from their height at $t_0$ because some of each layer has been removed, but the height of the underlayer peak will be dropping more quickly than the height of the top layer peak because of the difference in etch rates.

Figure 10C:
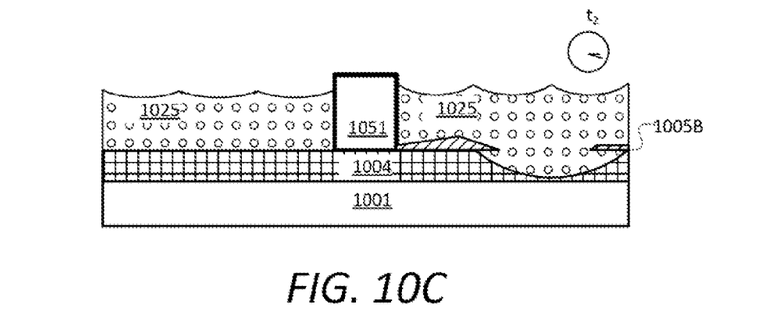

In FIG. 10C, at an even later time $t_2$, etchant 1025 has etched completely through uniform layer 1005A, laying bare the entire underlying part of underlayer 1004 at once. In the XRF measurement, the peak for top layer 1005A will be gone completely, and the peak for the part of underlayer 1004 underneath 1005A will be rapidly diminishing due to the fast etch rate. Meanwhile, some of the thickest parts of nonuniform top layer 1005B have not yet been etched through, and etchant 1025 continues to rapidly enlarge the undercut pit in underlayer 1004. In the XRF measurement, the peak for top layer 1005B will be small but still detectable; the peak for the part of underlayer 1004 underneath 1005B will be rapidly diminishing due to the fast etch rate, but perhaps not quite as rapid as the 1004 peak in the 1005A region, because some of the surface area of underlayer 1004 is still shielded by the remaining parts of top layer 1005B.

Figure 10D:
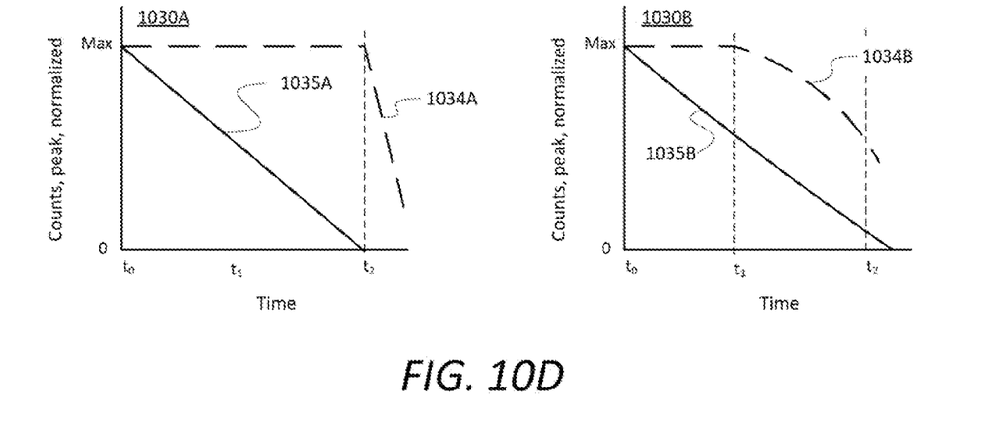

FIG. 10D shows the changes in peak heights with time in the two regions during the etch shown in FIGS. 10A-10C. For convenience, the peak heights are normalized to their maximum height Max, which in this example is the peaks' initial height at $t_0$. Graph 1030A represents the results for the region with uniform top layer 1005A. Line 1035A represents the height of the peak for top layer 1005A. Its height decreases linearly with time, at a rate related to the etch rate of etchant 1025 for the material of top layer 1005A, until it is completely etched through at time $t_2$. Line 1034A represents the peak for the underlayer 1004 in the region under top layer 1005A. Its height is constant at first, because it is not being etched, until $t_2$ when it begins to drop rapidly. The slope of the drop is constant because the entire region is exposed to the etchant.

Graph 1030B represents the results for the region with nonuniform top layer 1005B. Line 1035B represents the height of the peak for top layer 1005A. At time $t_2$, line 1035B does not go to zero because some of the high spots are not yet completely etched (see FIG. 10C). Line 1034B represents the peak for the underlayer 1004 in the region under top layer 1005B. Like line 1034A, its height is constant at first, because it is not being etched. However, line 1034B begins to drop at $t_1$ when the etchant breaks through the thinnest spot (see FIG. 10B), well before the corresponding top-layer peak 1035B disappears sometime after $t_2$. Line 1034B just after $t_1$ has a shallower slope than 1034A after $t_2$ because only a limited area is being exposed to the etching. The slope increases as more of the top layer is etched away and more of the underlayer is exposed. Some curves may have several "corners" where the slope increases as multiple thin spots are etched through.

Thus, by comparing characteristics of these curves, candidate top layers such as 1005A and 1005B may be screened for spatial uniformity. Besides thickness nonuniformity, the test may also reveal nonuniformities in composition or density.

To simplify this example, the limiting depth d for the XRF measurement was assumed to be at least the combined thickness of the thickest top layer and the underlayer (see FIG. 10A). However, it is possible to perform this test at a shallower limiting depth and take into account that the underlayer peak may initially grow as the top layer is etched, until either the bottom of the underlayer coincides with d or the etchant begins to etch the underlayer.

Figure 11:
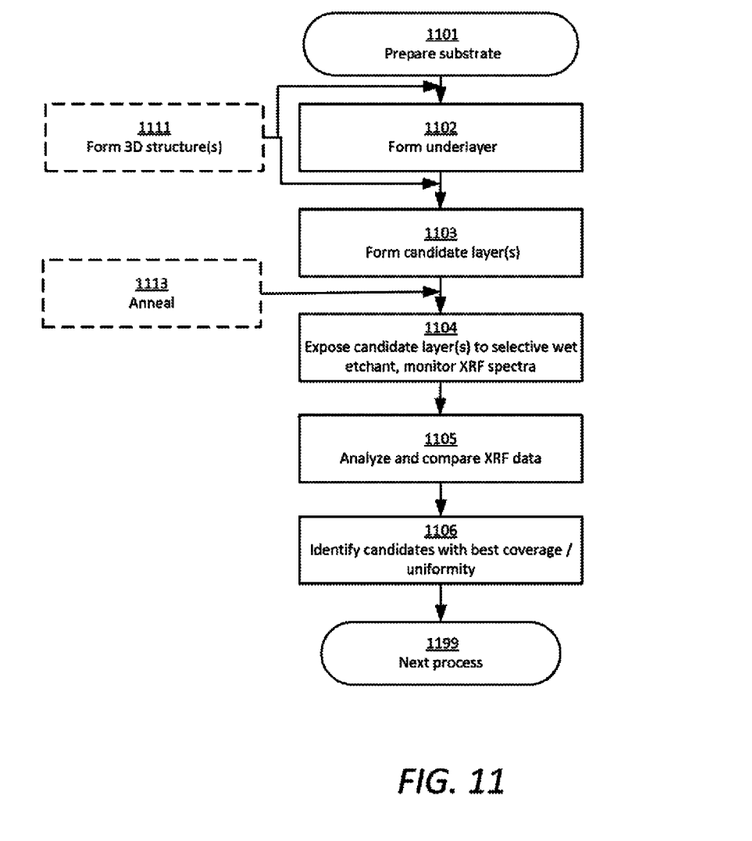
FIG. 11 is a flowchart of an example process for screening candidate layers by etch-XRF testing.

FIG. 11 is a flowchart of an example process for screening candidate layers by etch-XRF testing. Step 1101 of preparing a substrate may include cleaning, degassing, passivating, forming additional layers, or any other suitable process. Step 1102 of forming an underlayer may use any method suitable for the underlayer material, such as physical vapor deposition (PVD), evaporation, pulsed laser deposition (PLD), chemical vapor deposition (CVD), plasma enhanced chemical vapor deposition (PECVD), atomic layer deposition (ALD), plasma enhanced atomic layer deposition (PEALD), slurries, inks, pastes, sol-gels, printing, or any other method used in the art for the particular material.

Optionally, step 1111 of forming one or more 3D structures may follow either step 1101 (to form the structures on or in the substrate) or step 1102 (to form the structures on or in the underlayer). Any suitable patterning technique may be used, such as photolithography, laser scribing, ion milling, or spatially-controlled dry or wet etching. Characteristics of the 3D structures, such as dimensions, angles, and spacings, may be varied combinatorially across a single substrate or between separate substrates. In some embodiments of the method, the 3D structures are the sole variable, and the test determines limits of the top layer's ability to conformally coat structures with different characteristics.

Step 1103 of forming candidate (top) layers may involve forming at least two candidate layers, either on different site-isolated regions of a single substrate or on different substrates. In some embodiments, the candidate layers may be the same (e.g., to evaluate repeatability of the process of forming the layer, or to compare its conformality on different 3D structures). In some embodiments, the candidate layers may differ in composition or in the unit processes, process sequences, or details of the hardware used to form them.

Optional step 1113 of annealing the substrate may precede the etch/XRF test. Some types of cracks and islanding (e.g., agglomeration) are not present in layers as-deposited, but occur during annealing. Annealing times, temperatures, and atmospheres vary with the candidate layer's composition and intended purpose. For some types of materials, an interface layer can improve adhesion and prevent agglomeration during annealing. In some embodiments, the candidate layer may include a thin interface layer and the interface layer may be varied (in composition, thickness, presence/absence, method of formation, or some other parameter) between regions or substrates to evaluate the effects of different interface layers on agglomeration after annealing.

Step 1104 of exposing the candidate layers to a selective wet etchant while monitoring their XRF spectra may be done simultaneously for all the candidate layers or on one layer at a time. The selective wet etchant preferably etches the underlayer material faster than it etches any of the candidate layer materials. In some embodiments, the selective wet etchant etches the underlayer material more than 1.2× faster, more than 2× faster, more than 5× faster, more than 10× faster, or more than 100× faster than it etches any of the candidate layer materials. In some embodiments, the selective wet etchant does not measurably etch one or more of the candidate layer materials during the exposure time. Monitoring the XRF spectrum may include as few as two measurements (e.g., at the beginning and the end of the etch), many discrete measurements over the course of the etch, or continuous measurement.

In some embodiments, the design of an XRF/etch test may include calculating an etch time for which the etchant is expected to completely etch through an ideal top layer. As an example, the calculation may multiply the nominal etch rate of the etchant for the top-layer material(s) by the nominal thickness of the material: if the etchant etches material M at rate R (nm/minute) and the candidate top layers are intended to be X nm thick, etch time t=RX minutes. In the test, the etchant exposure may then be stopped before the calculated etch time.

Step 1105 of analyzing and comparing XRF data from the candidate layers may include examining the change in peak strength before and after etching (similar to FIG. 9), the changes in peak strength over time during the etching (similar to FIG. 10D), or any other useful analysis. More than one peak from the candidate layers or the underlayer may be analyzed. The multiple peaks may correspond to different transitions of electrons in the same element, or to different elements of a compound, such as the silicon and the oxygen in a silicon oxide. After step 1106 of identifying the candidate layers with the best coverage and/or uniformity, the next process 1199, such as another screening stage, may commence.

As an example, the candidate layer may be 3 nm thick tantalum nitride (TaN), the underlayer may be 250 nm thick silicon dioxide ($SiO_2$), the selective wet etchant may be buffered oxide etch (BOE), and the exposure time may be 1-15 min.

Other known selective wet etchants include the following:

| Etchant | Etches | Etches more slowly, or does not etch |
|---|---|---|
| Dilute HF | $HfO_x$ | $SiO_x$, $SiN_x$ |
| DSP + ($H_2SO_4/H_2O_2/HF$) | TiN | $HfO_x$, poly-Si |
| Non-aqueous HF/ethylene glycol | $HfO_2$ | $SiO_2$ |
| Heated dilute $NH_4OH/H_2O_2$ | TiN | Al |
| $NH_4OH/HF/H_2O_2$ | Cu, Ta, TaN | $SiO_2$ |

More information on these may be found in co-owned U.S. patent application Ser. No. 13/725,358 filed 21 Dec. 2012, Ser. No. 13/726,760 filed 26 Dec. 2012, Ser. No. 13/727,776 filed 27 Dec. 2012, Ser. No. 13/857,696 filed 5 Apr. 2013, and Ser. No. 13/913,672 filed 10 Jun. 2013, each of which is entirely incorporated by reference herein for all purposes. Many more selective wet etchants and associated materials are described in device-fabrication literature accessible to those working in the art.

From the above examples of using XRF to identify various events in the course of an etch process, it is understood that similar XRF data collection and analysis may be applied to other etching scenarios. For example, once calibrated, XRF may be used to monitor etch depth and detect the approach of desired endpoints in either prototype or production fabrication.

Figure 12:
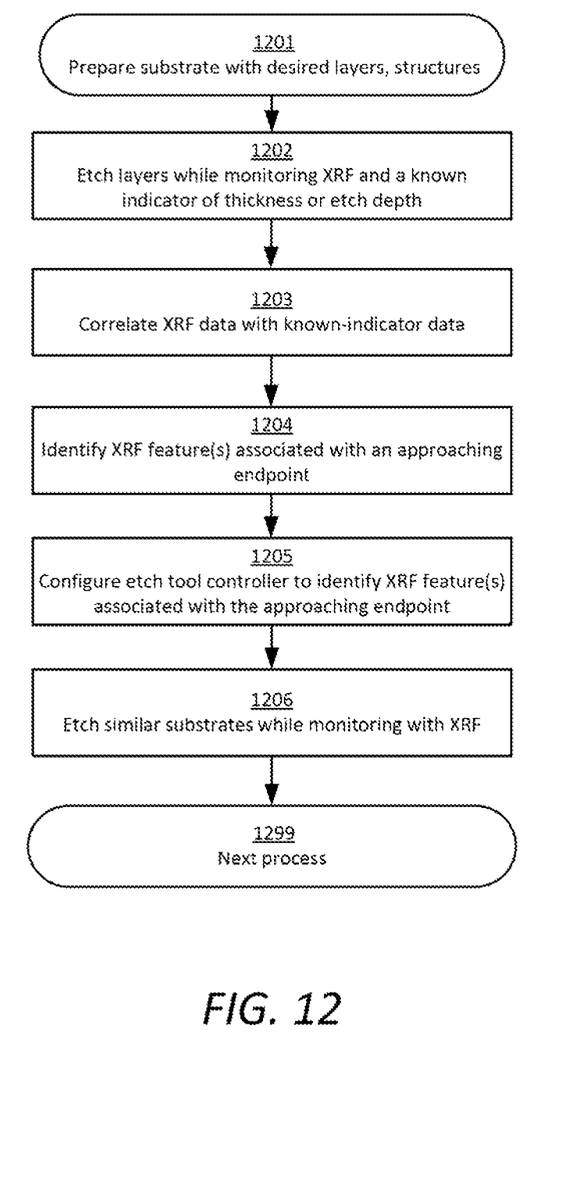
FIG. 12 is a flowchart of an example calibration process.

FIG. 12 is a flowchart of an example calibration process. Step 1201 of preparing the substrate includes forming all the layers and structures that precede the etch process of interest. In step 1202 of etching the layers while monitoring both XRF and a known indicator of thickness or etch depth, the known indicator may include interferometry, ellipsometry, or any other suitable known method.

In some embodiments, the calibration etch of step 1202 may go beyond a desired endpoint. For example, if the device design requires etching away 10 nm of material from a layer, the calibration etch may etch 15 nm. In some embodiments, however, the calibration etch may not exceed the desired endpoint; for example, if the device design requires etching away 10 nm of material from a layer, the calibration etch may etch 10 nm or less, such as 8 nm.

After the etch is complete, step 1203 of correlating the XRF data with the known indicator data may involve determining, from the known indicator data, the time when the endpoint was reached (if the calibration etch 1202 exceeded the endpoint) or the time when the endpoint would have been reached (if the calibration etch 1202 stopped short of the endpoint) and examining or extrapolating the XRF spectrum corresponding to the same time.

Step 1204 of identifying an XRF feature associates with an approaching endpoint may involve comparing an XRF spectrum collected at or before the endpoint with an initial XRF spectrum captured at the beginning of the etch. Alternatively, step 1204 may extrapolate the feature from a rate of change of one or more peak heights in the XRF spectrum. For example, the feature may be a particular peak height or a particular rate of change in a peak height. The feature may occur at the endpoint or some time before the endpoint; that is, the XRF spectrum preceding the endpoint may be analyzed to find any "early warning" markers such as a sudden change in the height of a peak or its rate of change.

Step 1205 of configuring a controller for an etch tool to detect XRF features associated with the approaching endpoint may include storing one or more of the measured spectra, configuring hardware to receive XRF data, or programming algorithms or heuristics to detect measured characteristics corresponding to an endpoint or an event preceding the endpoint and stop the etch process when or after the characteristics are detected. If the feature coincides with the endpoint, the tool may immediately stop etching when the feature is detected. If the feature precedes the endpoint by a known time period (e.g., 10 seconds), the tool may be programmed to continue the etch for that amount of time before stopping.

Although the foregoing examples have been described in some detail to aid understanding, the invention is not limited to the details in the description and drawings. The examples are illustrative, not restrictive. There are many alternative ways of implementing the invention. Various aspects or components of the described embodiments may be used singly or in any combination. The scope is limited only by the claims, which encompass numerous alternatives, modifications, and equivalents.

What is claimed is:

1. A method, comprising:
forming an underlayer over a substrate;
forming a top layer over the underlayer;
exposing the top layer to an etchant, wherein the etchant etches the underlayer more rapidly than the top layer;
collecting a plurality of XRF measurements, wherein at least one of the XRF measurements is collected after the exposing begins; and
determining a coverage or uniformity characteristic of the top layer from the XRF measurements.

2. The method of claim 1, further comprising annealing the substrate after the forming of the top layer and before the exposing to the etchant.

3. The method of claim 1, further comprising:
calculating an etch time at which the etchant is expected to etch through an ideal top layer; and
stopping the exposing before the etch time elapses.

4. The method of claim 1, wherein the coverage or uniformity characteristic comprises one of pinholes, cracks, islands, sidewall gaps, thickness non-uniformity, density non-uniformity, or composition non-uniformity.

5. The method of claim 1, wherein the XRF measurements comprise a height difference in a peak associated with the underlayer before and after the exposing to the etchant.

6. The method of claim 1, wherein the XRF measurements comprise a height difference in a peak associated with the top layer before and after the exposing to the etchant.

7. The method of claim 1, wherein the XRF measurements comprise a time when a peak associated with the underlayer changes in height.

8. The method of claim 7, wherein the XRF measurements comprise a height of a peak associated with the top layer at the time when the peak associated with the underlayer changes in height.

9. The method of claim 1, wherein the XRF measurements comprise multiple peaks produced by one of the underlayer or the top layer.

10. The method of claim 1, wherein the substrate or the underlayer comprises a 3D structure.

11. The method of claim 10, wherein the 3D structure comprises at least one of a pillar, a ridge, a trench, or a via.

12. The method of claim 10, wherein the coverage or uniformity of the top layer comprises conformality to the 3D structure.

13. The method of claim 1, wherein the top layer comprises an interface layer in contact with the underlayer.

14. The method of claim 1, wherein the underlayer comprises silicon dioxide and the top layer comprises tantalum nitride.

15. The method of claim 14, wherein the etchant comprises buffered oxide etch (BOE).

16. The method of claim 15, wherein the top layer is exposed to the etchant for between 1 minute and 15 minutes.

17. The method of claim 1, wherein the underlayer comprises hafnium oxide and the top layer comprises silicon oxide or silicon nitride.

18. The method of claim 17, wherein the etchant comprises dilute hydrofluoric acid.

* * * * *